[![](](

United States Patent
Wendler

(10) Patent No.: US 9,286,732 B2
(45) Date of Patent: Mar. 15, 2016

(54) NUCLEAR IMAGE SYSTEM AND METHOD FOR UPDATING AN ORIGINAL NUCLEAR IMAGE

(71) Applicant: SurgicEye GmbH, Munich (DE)

(72) Inventor: Thomas Wendler, Munich (DE)

(73) Assignee: SURGICEYE GMBH, Munich (DE)

( * ) Notice: Subject to any disclaimer, the term of this patent is extended or adjusted under 35 U.S.C. 154(b) by 29 days.

(21) Appl. No.: 14/344,972

(22) PCT Filed: Sep. 17, 2012

(86) PCT No.: PCT/EP2012/068251
§ 371 (c)(1),
(2) Date: Mar. 14, 2014

(87) PCT Pub. No.: WO2013/038011
PCT Pub. Date: Mar. 21, 2013

(65) Prior Publication Data
US 2014/0369560 A1   Dec. 18, 2014

(30) Foreign Application Priority Data
Sep. 16, 2011   (DE) .......................... 10 2011 053 708

(51) Int. Cl.
*G06K 9/00* (2006.01)
*G06T 19/20* (2011.01)
(Continued)

(52) U.S. Cl.
CPC .............. *G06T 19/20* (2013.01); *A61B 6/4258* (2013.01); *A61B 6/5205* (2013.01); *A61B 6/547* (2013.01);
(Continued)

(58) Field of Classification Search
CPC ............... G06T 7/0012; G06T 7/0016; G06T 2207/30004; G06T 2207/10104; G06T 2207/10108; G06K 2209/057; A61B 5/1128; A61B 5/0033; A61B 6/46; A61B 2576/00; A61B 1/00009; A61B 6/52; A61B 6/035; A61B 6/5294; A61B 8/5207; A61B 8/52
See application file for complete search history.

(56) References Cited

U.S. PATENT DOCUMENTS 7,826,889 B2    11/2010  David et al.
2004/0015075 A1*  1/2004  Kimchy et al. ............... 600/424
(Continued)

FOREIGN PATENT DOCUMENTS

DE    10 2008 025 151 A1    12/2008

OTHER PUBLICATIONS

International Search Report and Written Opinion dated Feb. 19, 2013 for Application PCT/EP2012/068251.

*Primary Examiner* — Avinash Yentrapati
(74) *Attorney, Agent, or Firm* — Moser Taboada

(57) ABSTRACT

A nuclear image system for updating an original nuclear image, the nuclear image system comprising: a data memory for storing the original three-dimensional nuclear image; a nuclear radiation detector, which is movable along a freely variable path, for measuring nuclear radiation, in order to obtain nuclear radiation values; a tracking system for tracking the nuclear radiation detector while measuring the nuclear radiation, so that detector coordinates are obtained which indicate a posture of the tracked nuclear radiation detector in relation to an image coordinate system of the nuclear image; a nuclear data input configured to receive the nuclear radiation values from the nuclear radiation detector and the detector coordinates from the tracking system, and to associate the nuclear radiation values with the respective detector coordinates; and an image updating module including an updating rule for changing the original nuclear image on the basis of the nuclear radiation values and the detector coordinates, wherein the image updating module is configured to generate an updated three-dimensional nuclear image by applying the updating rule to the original nuclear image.

7 Claims, 8 Drawing Sheets

(51) Int. Cl.
| | |
|---|---|
| *A61B 6/00* | (2006.01) |
| *G01T 1/164* | (2006.01) |
| *G01T 1/16* | (2006.01) |
| *G06T 7/00* | (2006.01) |
| *G06T 7/20* | (2006.01) |
| *A61B 6/03* | (2006.01) |
| *A61B 6/04* | (2006.01) |

(52) U.S. Cl.
CPC . *G01T 1/16* (2013.01); *G01T 1/164* (2013.01); *G01T 1/1648* (2013.01); *G06T 7/0012* (2013.01); *G06T 7/0079* (2013.01); *G06T 7/204* (2013.01); *A61B 6/037* (2013.01); *A61B 6/0492* (2013.01); *A61B 6/5235* (2013.01); *G06T 2207/10104* (2013.01); *G06T 2207/10108* (2013.01); *G06T 2207/30004* (2013.01); *G06T 2207/30196* (2013.01); *G06T 2207/30204* (2013.01)

(56) References Cited

U.S. PATENT DOCUMENTS

| | | | |
|---|---|---|---|
| 2004/0054248 A1* | 3/2004 | Kimchy et al. | 600/3 |
| 2005/0055174 A1* | 3/2005 | David et al. | 702/152 |
| 2008/0230704 A1 | 9/2008 | Daghighian | |
| 2010/0266171 A1* | 10/2010 | Wendler et al. | 382/128 |
| 2012/0018641 A1 | 1/2012 | Watanabe et al. | |
| 2014/0369560 A1* | 12/2014 | Wendler | 382/103 |

* cited by examiner

NUCLEAR IMAGE SYSTEM AND METHOD FOR UPDATING AN ORIGINAL NUCLEAR IMAGE

The invention belongs to the field of nuclear imaging, such as PET or SPECT, and aspects of the invention relate to a device for updating an original nuclear image on the basis of the measured data of a freely movable, tracked nuclear radiation detector. Further aspects of the invention relate to a corresponding method for updating the original nuclear image.

Various methods for nuclear imaging, such as PET and SPECT imaging methods, are known. These methods allow radioactive radiation sources emitted by a body to be rendered spatially resolved, e.g. as a three-dimensional nuclear image (radiation distribution image). This enables the distribution of a radiopharmaceutical in the body to be identified, for example in order thus to derive conclusions on the function and/or metabolism processes of various organs or regions in the body. These methods allow the reliable assessment of various cancers and localization of the affected tissue. This information has a high utility value for surgical interventions, e.g. to remove infected tissue.

Many of these imaging methods require a nuclear detector to be stationary or movable along a fixed trajectory, such as in conventional PET and SPECT methods. However, if such a detector is to deliver sufficient information for a nuclear image of good quality, it should at least in principle be able to detect the radiation leaving the person to be imaged in directions as different as possible. Document US 2010174498 A1 for instance describes such a nuclear detector, in which a patient's bed can be moved into a PET gantry, to generate a nuclear image. Such a nuclear detector, however, requires a considerable amount of space and complicates access to the person to be imaged. For this reason, such a detector can only be used with difficulty, if at all, in a surgical environment. However, if it is used outside, the image may inevitably be no longer up to date, e.g. due to intermediate movements of the person to be imaged.

So-called freehand nuclear detectors, such as freehand SPECT detectors for instance, are based on a fundamentally different approach: here, a nuclear probe (typically a detector for nuclear radiation with a collimator connected upstream thereof) is freely movable, i.e. at least locally movable, albeit in a limited spatial area, in all three spatial directions and, as a rule, also rotatable with respect all three solid angles. These freehand nuclear detectors allow radiation to be detected from different directions with respect to the person to be imaged, without being an impediment, and can therefore also be used in a surgical environment, without any problems. Such freehand nuclear detectors are described in DE 10 2009 042 712 A1 for instance.

Tracking techniques are of particular importance for these freehand nuclear detectors, and these tracking techniques form in part the basis of completely novel imaging methods. Thus, by using tracking techniques, various medical imaging methods, such as nuclear magnetic resonance, SPECT, optical or PET imaging, can also be performed with hand-held probes in situations where this would otherwise not be possible. In doing so, a tracking system is used, which allows objects used in the imaging method, such as radiation detectors for example, to be tracked as target objects. i.e. In order to detect their posture (three space coordinate allocation and two or three angle coordinate allocation indicating the orientation) in particular within their time dependence. Herein, a medical application is generally designated as an operation, i.e. surgical operations in a more restricted sense are only a partial field of what is herein more generally referred to as an operation. In addition, an imaging method or preparative or supportive actions for a surgical operation for example are also understood here as an operation. In such a case, tracking is performed in a surgical environment or a part thereof. In general, a surgical environment should be understood as an environment in the area of which medical applications, such as a surgical operation, an imaging method, parts of a diagnostic process, and the like are to take place. For example, the surgical environment may be a part of an operating room, in particular an area for a patient to be operated on. Even though the application of a surgical operation by a surgeon will be particularly emphasized hereinafter, further embodiments may be directed at other medical applications, e.g. applications for methods of guiding instruments or tracked imaging methods.

As compared to conventional methods, the tracked freehand imaging methods, however, are performed in part under less controlled conditions. Whether an image of good quality can be obtained, also significantly depends on the user's experience and moreover can take an increased amount of time. In the event of intra-operative imaging, the surgical environment will be occupied during this time.

Against this background, a nuclear image system for updating an original nuclear image according to claims 1 and 2 and a corresponding method according to claims 10 and 11 are therefore proposed. Further preferred aspects of the invention will result from the dependent claims, the figures, and the description.

A nuclear image system allows a nuclear image to be generated without boundary conditions having to be taken into consideration, which have to be observed with a nuclear image to be taken directly in a surgical environment, in particular the accessibility of the surgical environment. This original nuclear image may not describe any most recent changes, such as intermediate movements of the person to be imaged or within the person to be imaged (e.g. of organs in the body), changes in the radiation source (the radiopharmaceutical) in the body, and the like. This disadvantage is however compensated for, in that current measurements of the nuclear radiation and/or current position measurements of the patient are enabled by a freely movable nuclear radiation detector. The image updating module enables the original nuclear image to be changed and thus the up-to-date information to be taken into consideration and incorporated into the updated image.

Herein, a radiation distribution image is understood as a nuclear image, i.e. a three-dimensional intensity distribution (e.g. a radiation distribution image, i.e. a reconstructed radiation intensity as a function of the three spatial coordinates X, Y, Z) obtained from a nuclear measurement. Intensities other than the reconstructed radiation intensity can also be mapped on a nuclear image, e.g. absorption intensity with respect to nuclear beams. Even data resulting in a three-dimensional intensity distribution after decoding or other real-time processing may be understood as a nuclear image.

The invention also relates to a device for executing the disclosed methods and comprises device parts for executing respective single process steps. The method steps may be executed by hardware components, by a computer programmed by means of a corresponding software, by a combination of both or in any other manner. The invention is furthermore also directed at methods according to which the respective described devices operate. Included are method steps for executing each function of the devices. One potential aspect of the invention also relates to the nuclear image system described herein for use in intra-operative nuclear imaging.

Hereinafter, the invention will be described on the basis of exemplary embodiments illustrated in figures, from which further advantageous parts and modifications will result.

Figure 7:
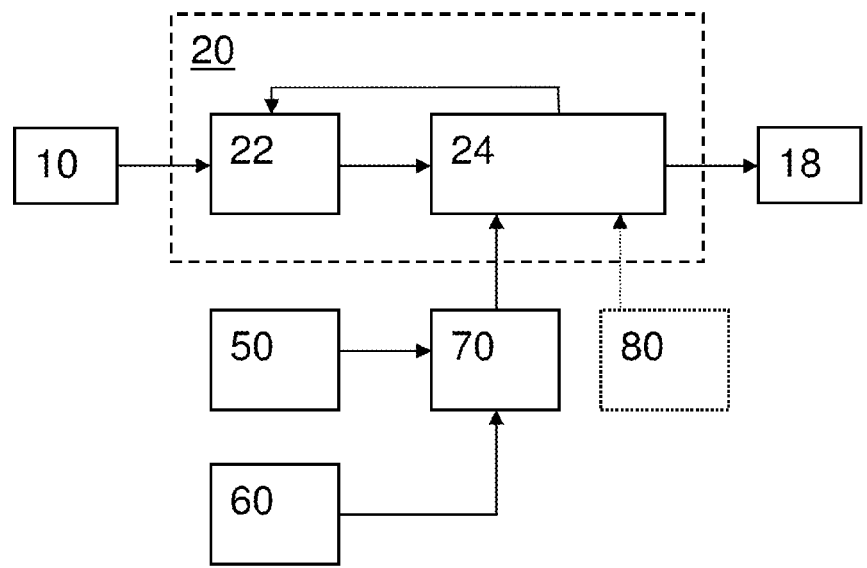
FIG. 7 shows a diagrammatic representation of the functionality of a nuclear image system according to an embodiment of the invention.
Figure 10:
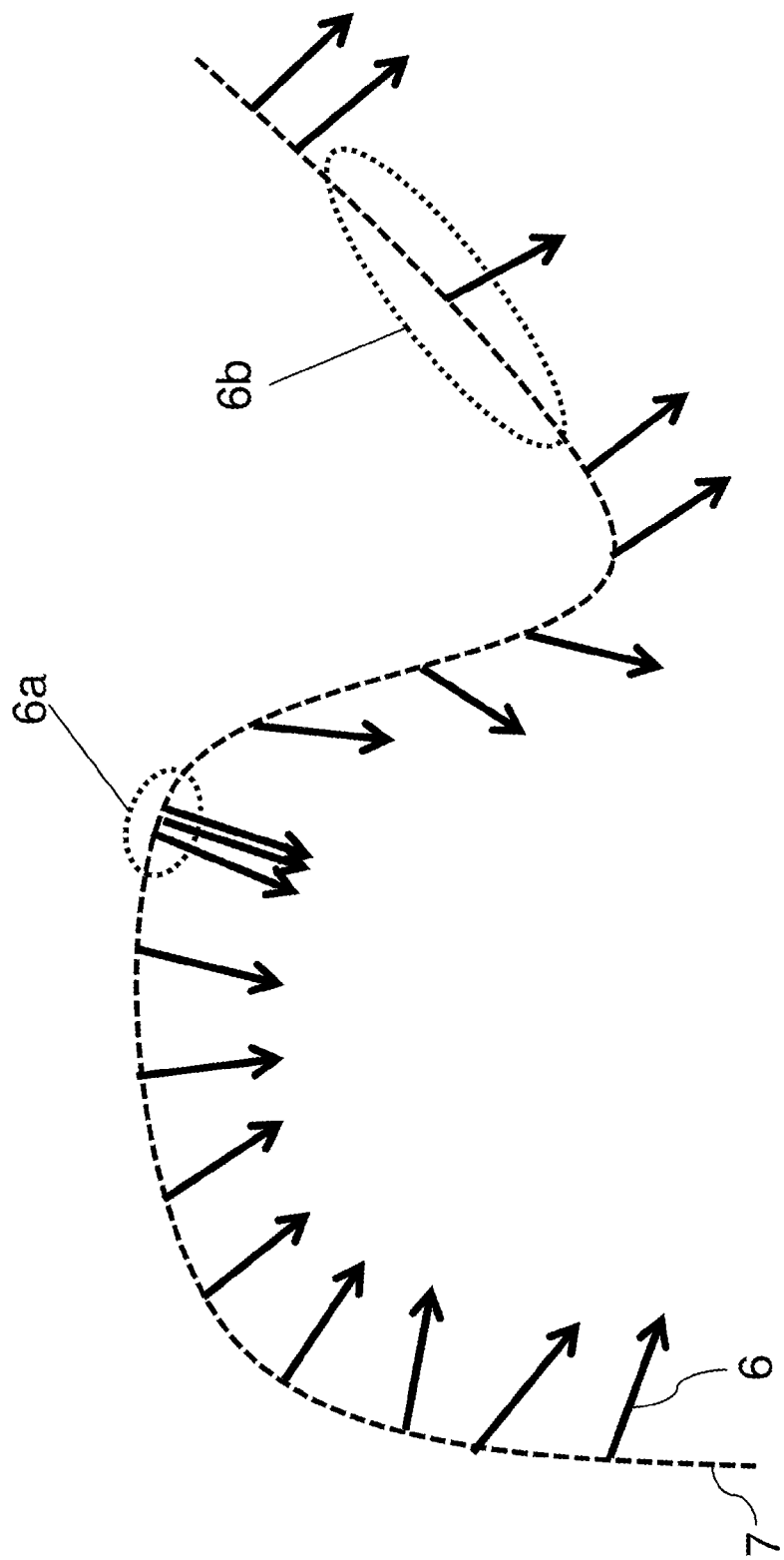
Figure 11:
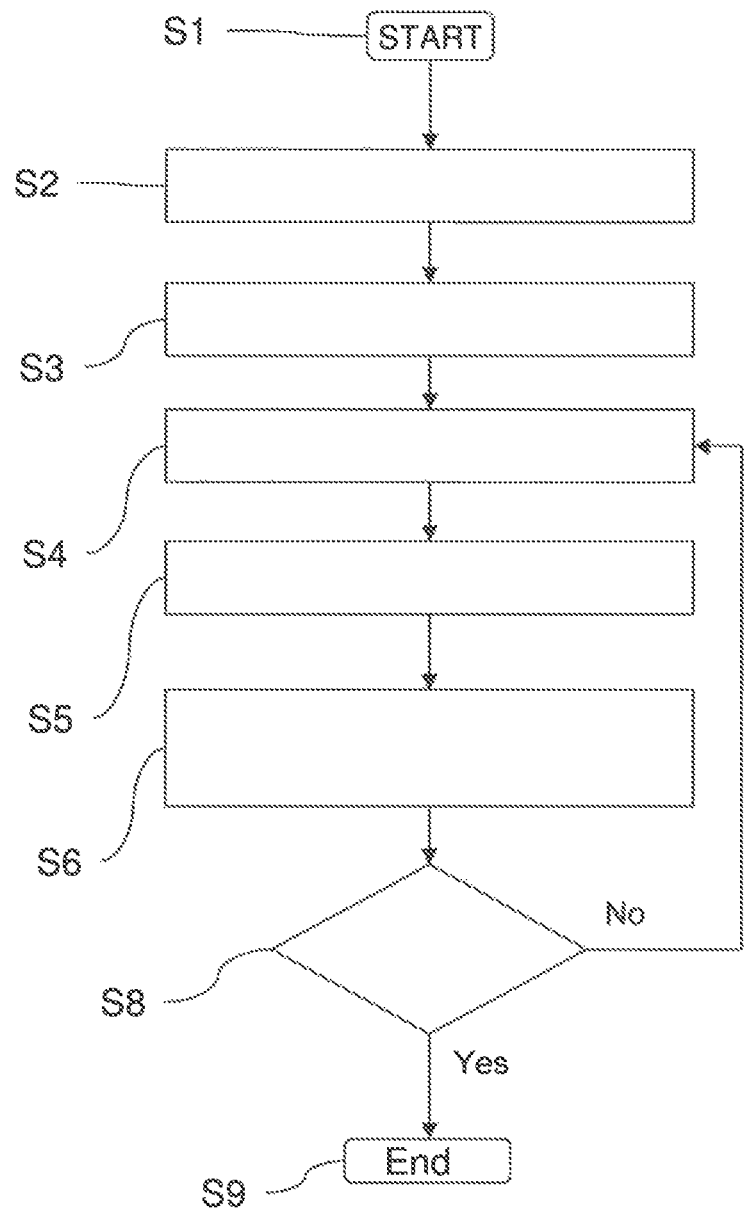
Figure 12:
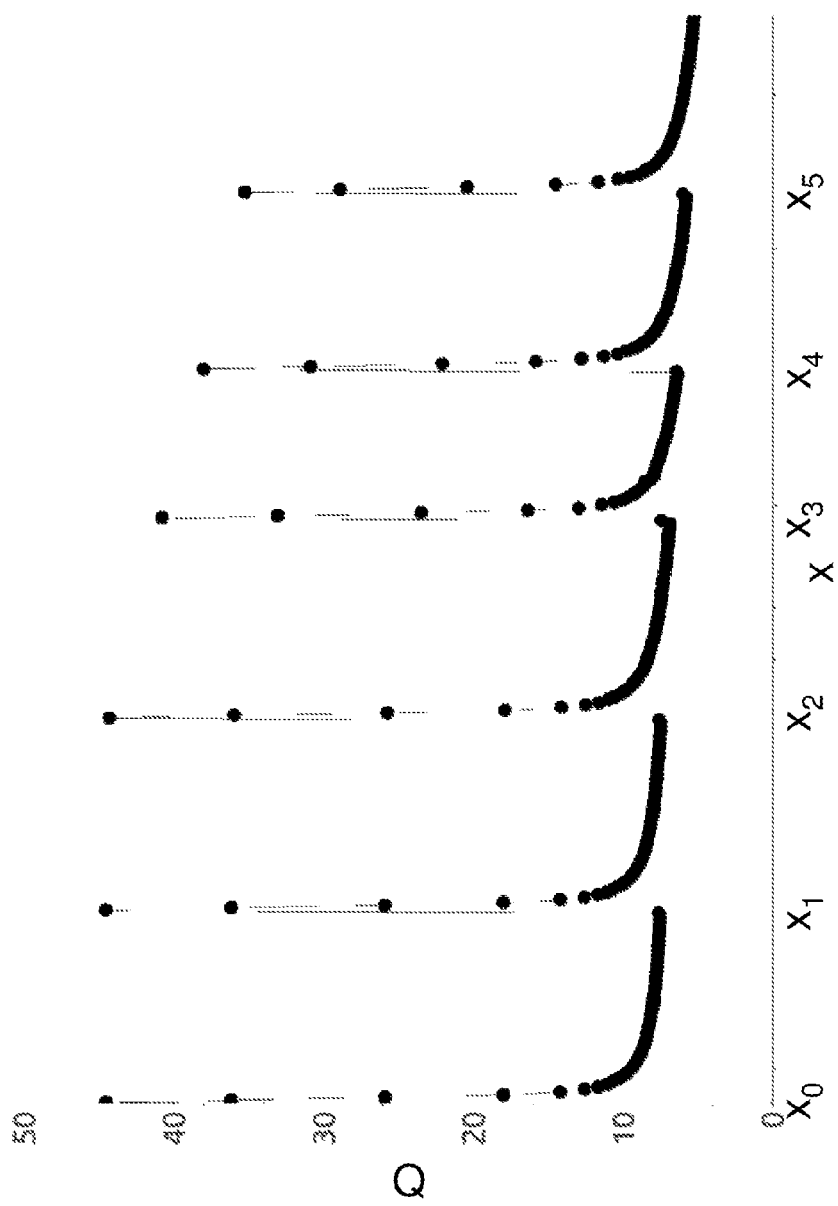

FIG. 10 schematically shows a method for eliminating nuclear image information for the nuclear image system of FIG. 7;

FIG. 11 shows a flowchart including the steps of a method for updating an original nuclear image according to an embodiment of the invention; and FIG. 12 shows a diagram representing a quality value Q as a function of an iteration value x in the method of FIG. 11.

Various embodiments of the invention will be described hereinafter, some of which are also shown in the figures as examples. In the following description, identical reference numbers refer to identical or similar components. In general, only differences between different embodiments will be described. In this case, features described as a part of an embodiment may also be easily combined in connection with other embodiments so as to generate still further embodiments.

Figure 1:
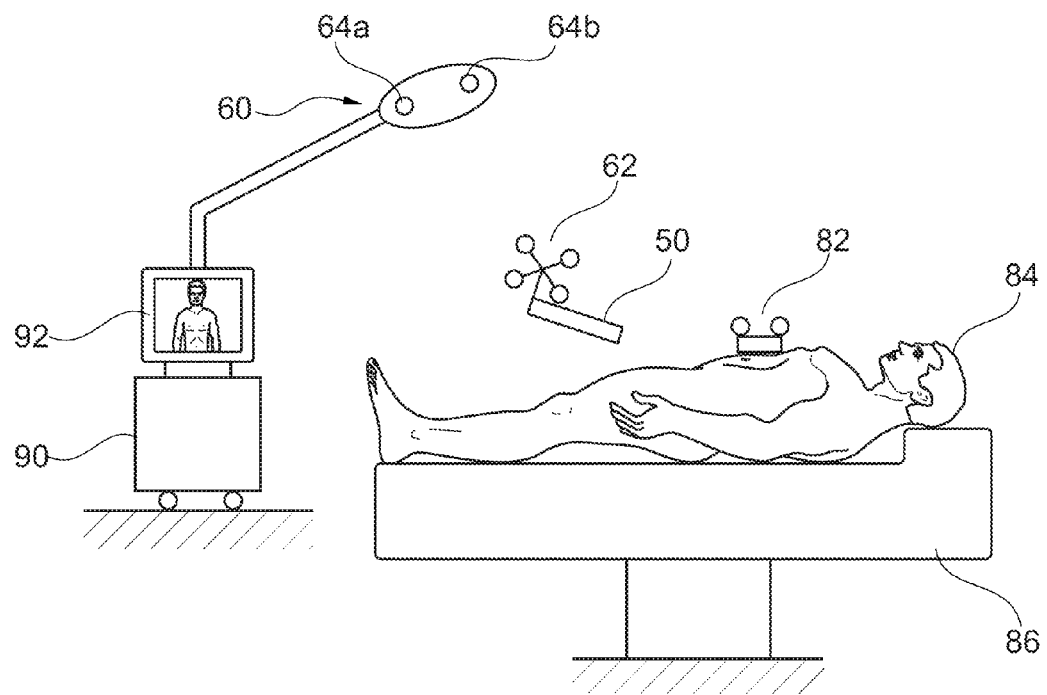
FIG. 1 shows a device for 3D acquisition and 3D visualization.

FIG. 1 shows parts of a nuclear image system according to a first aspect of the invention, which is able to update a stored original nuclear image. The original nuclear image in the situation illustrated in FIG. 1 has already been taken and is stored in a data memory e.g. in the data acquisition system 90.

The original nuclear image is a complete, three-dimensional nuclear image, which was reconstructed on the basis of a previous measurement. The measurement can be performed by means of the system illustrated in FIG. 1; alternatively, the original nuclear image can also be generated by a separate system (e.g. by means of a nuclear detector which is not freely movable, and thus stationary or movable along a defined trajectory). The original nuclear image reflects a spatial distribution of the radiation intensity of a radiation source, e.g. the radiation intensity as a function of respective voxels. An image coordinate system of the nuclear image will hereinafter be referred to as KN.

Furthermore, a nuclear radiation detector 50 for measuring nuclear radiation is shown in FIG. 1. The nuclear radiation detector 50 is movable along a freely variable path, is thus movable at least locally in all three spatial directions, and in this case also rotatable with respect to all three solid angles. Further examples for a detector which is freely movable along a freely variable path are e.g. a detector mounted on a controllable robot arm and having sufficient degrees of freedom, a detector which is freely displaceable and height-adjustable during measurement, and the like.

The nuclear radiation detector 50 comprises a collimator, which only selectively allows radiation from a given angular range to enter and to pass, and a detector behind it in the beam direction, in order to obtain nuclear radiation values, to be more precise, a measured radiation intensity or frequency as a function of time. Optionally, the nuclear radiation detector 50 comprises an energy filter, to filter nuclear radiation energetically prior to the detection.

In general, the nuclear radiation detector may be a detector of dimension 0, 1 or 2. In this case, a detector of dimension 0 is configured such as to allow a single radiation value in the detector volume to be measured at a given time. One example of this is a single gamma probe, if need be with a collimator mounted in front. Dimension 1 means that the detector allows space-resolved measurement along a one-dimensional line; and dimension 2 means that the detector allows space-resolved measurement in both directions of a 2D surface. One example of a 2D sensor is a gamma camera. An analog of a 2D sensor in the case of an optical sensor would be a CCD sensor for example. In addition, further space resolution may be performed by moving the detector and time-dependent measuring.

The detector may be e.g. a nuclear probe, a nuclear camera, a coincidence camera, a Compton camera or a combination thereof.

In general, it is a freehand detector, and the detector is configured to be manipulated by one hand and exhibits a handle portion for gripping and holding the detector in one hand. Optionally, a detector holder which keeps the detector in a defined position even when released, may be made available.

The nuclear radiation detector 50 may moreover include a data interface for transmitting measured data to an appropriate data acquisition system 90, e.g. an appropriate computer. Parts of the nuclear radiation detector 50, such as parts of the detector element, may also be accommodated to be spatially separated from the remaining nuclear radiation detector 50.

FIG. 1 moreover shows a tracking system 60, which serves the purpose of tracking the nuclear radiation detector 50 during the measuring of nuclear radiation and will be described hereinafter. Here, tracking means the time-dependent detecting of the posture (orientation) of the nuclear radiation detector 50, i.e. its spatial position and orientation. The position is described by means of three detector coordinates for specifying the position in three-dimensional space; and the orientation is usually described by means of three detector solid angles. In some embodiments, however, two solid angles will suffice, i.e. when a rotation of the detector will have no effect anyway on the measurement, such as is the case e.g. in certain 0-dimensional detectors.

The tracking system shown in FIG. 1 is an optical tracking system. For this system, an optical tracking target object 62, including optical marks, is fixed to the nuclear radiation detector 50. On the basis of the relative positions of the marks, which can be recorded by means of a stereoscopic camera 64a, 64b, the position and orientation (posture) of the nuclear radiation detector 50 can be estimated in real time with great precision. This posture can be expressed in a detector coordinate system, hereinafter referred to as KD.

The tracking system is equipped to detect and indicate the posture of the nuclear radiation detector 50 (coordinate system KD) in relation to the original nuclear image (coordinate system KN). For this purpose, the tracking system is adapted to establish a spatial relationship between systems KD and KN. In the embodiment of FIG. 1, this is achieved by attaching a further tracking target object 82 to the person 84 to be imaged.

The position or posture of the tracking target object 82 in the nuclear image coordinate system KN is known (e.g. by calibration) or has been calculated at the beginning of the procedure, by registration. The tracking target object 82 for instance may already be attached to the person 84 during the recording of the original nuclear image, and the nuclear image detector used in this case be equipped with a further tracking target object (analogous to the tracking target object 62), in order to register the tracking target object 82 in the nuclear image coordinate system KN, i.e. to establish a relationship between the position of the tracking target object 82 and the nuclear image coordinate system KN. More generally, the registration may be performed as a point-based registration, surface-based registration, image-based registration (such as by means of image recognition which brings "landmarks" in correspondence, which are recognizable in the image), or a combination thereof.

Due to the tracking system 60 now also detecting the posture of the tracking target object 82 in the detector coordinate system KN, the relationship (coordinate transformation) between KD and KN can be assessed in a manner known to a person skilled in the art. On the basis of this relationship, the detector coordinates also indicate the posture of the nuclear radiation detector 50 in relation to the image coordinate system of the nuclear image. To this effect, it is not necessary to actually convert the detector coordinates into coordinates of the nuclear image coordinate system KN; the existence of a reproducible relationship or transformation between KD and KN, in this case one established by the tracking target object 82, will suffice.

In this embodiment, the stereoscopic camera 64a. 64b may optionally be moved, including time-dependently, and does not need to be tracked itself as long as both tracking target objects are in its view since it is sufficient to know the posture of these two tracking target objects 62 and 82 in any common coordinate system, in order to calculate the posture of the detector 50 in relation to a nuclear image coordinate system KN (definable by means of the tracking target object 82), e.g. as a relative posture or differential posture. Alternatively, the stereoscopic camera may be focused fixedly on one of the tracking target objects.

Like the measured values of the nuclear probe 50, the tracking information (time-dependent posture) is also transmitted to the data acquisition system 90 by means of a data interface (not shown). The data acquisition system 90 has a nuclear data input for receiving both the nuclear radiation values from the nuclear radiation detector 50 and the detector coordinates (posture) from the tracking system 60. The nuclear data input also comprises a synchronizing module which is able to associate the nuclear radiation values with the respective detector coordinates. For this purpose time stamps, which are provided in the nuclear radiation values and the detector coordinates for example, may be compared and parameters, which have occurred in a common time slot, associated with one another. As an alternative, the posture associated with a determined nuclear radiation value may also be assessed by interpolating temporally adjacent measured postures. This association is generally referred to as a synchronizing of the nuclear radiation values with the detector coordinates (detector posture).

As a general aspect, the measured nuclear radiation values taken alone do not necessarily allow the complete 3D reconstruction of the nuclear image. Yet they are useful for updating the stored original image, as will be described hereinafter.

The updating of the stored original nuclear image will now be described in more detail with reference to FIG. 7. The updating is performed by an image updating module 20 which may be implemented for example as a program running on a computer 90 (see FIG. 1). Moreover, the following elements already described above are illustrated in FIG. 7: nuclear radiation detector 50, tracking system 60, and nuclear data input 70 including the synchronizing module for allocating the nuclear radiation values to the respective detector coordinates.

The image updating module 20 includes an updating rule for changing the original nuclear image 10 stored in the data memory, based on the nuclear radiation values and detector coordinates, and thus to obtain an updated three-dimensional nuclear image 18 in which information gained from the measured data is taken into account. The image updating module 20 thus generates an updated three-dimensional nuclear image 18 by applying the updating rule to the original nuclear image 10.

To this effect, the image updating module 20 includes an image varying function 22 and an image quality functional 24. The image quality functional 24 accesses the nuclear radiation values (to be more precise, the data set comprising the nuclear radiation values and the associated detector postures) from the nuclear data input 70 and the nuclear image. This may be the original nuclear image or an already varied nuclear image. The image quality functional 24 calculates an image quality value (as a real number) from these input parameters and, if necessary, further parameters, which quality value indicates the quality of the nuclear image with respect to the newly measured nuclear radiation values. An exemplary implementation of an image quality functional 24 is described further below, in which a low image quality value expresses the high quality of the nuclear image. In this hereinafter assumed case, the image updating module 20 is implemented such that the nuclear image 10 is varied so as to approximate a minimum of the image quality functional 24. However, an equivalent implementation with obvious changes is also possible, in which a high image quality value expresses the high quality of the nuclear image and a maximum is approximated.

The image varying function 22 serves the purpose of varying the nuclear image 10 (or of an already varied nuclear image), based on the number of arguments or parameters which may also be random parameters. An exemplary implementation of an image varying function 22 is described further below.

The image updating module 20 accesses the original nuclear image 10 and varies it while using the image varying function 22, so that the result approximates a minimum of the image quality function 24 (within the framework of the nuclear images that can be generated by the image varying function 22). Depending on the image quality functional 24, this can be done in some cases by a precise calculation, but as a rule may be achieved in the most efficient manner by an iterative method. In this case, the image varying function 22 is applied consecutively multiple times to the original nuclear image 10 or recursively to the previously obtained and stored varied nuclear image. Alternatively, the image varying function is applied again and again to the original nuclear image 10, with the parameters of the image varying function 22 being adjusted iteratively, such that the minimum is gradually approximated. The nuclear image 10 may in this case be varied in a merely indirect way, by only varying the image varying function 22 and expressing the image quality functional 24, based on these parameters. Such a variation of only these parameters can also be considered as a(n) (indirect) variation of the nuclear image since the nuclear image can be obtained from the parameters by the image varying function 22 at any time.

If the number of arguments of the image varying function is large, a high-dimensional minimizing problem is present. Iterative algorithms for efficiently solving such problems, such as the method of conjugated gradients, the Simplex method, and the method of simulated annealing, are known and for example described in the publication "Numerical Recipes" (available at http://www.nr.com). Further methods are the Monte Carlo-based or Random Walk methods. By means of these or further methods, the image updating module 20 varies the (original or already varied) nuclear image 10 iteratively using the image varying function 22, so that the resulting nuclear image gradually approximates a minimum of the image quality functional 24. When the iterations are completed, the finally resulting nuclear image is output as the updated nuclear image 18.

Herein, the following nomenclature is also used:

| Parameter | Symbol | Description |
| --- | --- | --- |
| Nuclear image 10, 18 | V | X*Y*Z* voxels in the coordinate system KN (reconstructed intensity distribution) |
| Image varying function 22 | T, T(V) | Mapping T: V -> T(V); T(V) is the varied nuclear image (X*Y*Z* voxels, coordinate system KN). T depends on further transformation parameters. |
| Nuclear data | b, b(i) | Vector of length N (= number of measurements), i = 1 ... N, with the values b depending on the detector's dimension d being numerical values (d = 0) or arrays of dimension d (d = 1, 2) |
| Posture | $\underline{p}$, $\underline{p}(i)$ | For each measurement p(i) the associated posture indications (position and orientation of the nuclear detector) in a coordinate system KD whose relation to KN is known. |
| Projection | P(V) or P($\underline{p}$, V) | Outputs associated nuclear data b = P(V) for a nuclear image V which should be measured by a detector having the postures $\underline{p}$. Since P here is only of interest for a given posture (the measured posture $\underline{p}$), the dependence of the projection on posture $\underline{p}$ will not be further mentioned explicitly. |
| Quality functional | Q(V, $\underline{p}$, b) | Renders a real number, see e.g. Eq. (1) below |

The algorithm described above and represented in FIG. 7 calculates the resulting nuclear image Vr as a minimum. Vr=argmin$_T$ Q(T(V),$\underline{p}$,b) using this nomenclature.

The image quality functional 24, Q(T(V),$\underline{p}$,b), can be implemented as follows:

$$Q(T(V),\underline{p},b) = \|P(\underline{p},T(V))-b\|_{L2} = \Sigma_i (P(\underline{p},T(V))(i)-b(i))^2 \qquad (1)$$

This functional is calculated from the nuclear radiation values and also from the posture, and indicates the deviation of the measured nuclear data b from the expected or simulated measured data P($\underline{p}$, V) of the nuclear image V. A low image quality value thus expresses the high quality of the nuclear image. Instead of the L2 norm used in (1), any other functions for calculating a deviation may be used as well, e.g. any L norm, any correlation function or the like.

Further expansions to equation (1) are possible. For instance, a regularization term R(T) may be further added to the above image quality functional (1). Such a regularization term R(T) can express the plausibility of a certain image transformation. The regularization term R(T) for example can output an increased value for the image transformations T, which excessively distort the nuclear image (the argument T in the expression R(T) represents a set of parameters which determine the image transformation function T). Such a regularization term may be interpreted physically as the elasticity of the image transformation since severe distortions are suppressed. In this or a similar manner, various model assumptions regarding potential image distortions may be implemented, for instance the conservation of mass, conservation of activity, elasticity, and potential changes of a tracer within the human body. These models may in particular include physical models of possible deformations within the human body, such as discrete models (e.g. particle and spring models) or continuous models (e.g. hyperelasticity models). The regularization terms may also take further internal information into consideration, such as tracer or radioactivity changes within the body, which have occurred in the interim (e.g. the amount of additionally injected tracer, amount of tissue that has already been removed, etc.). Such regularization terms also allow a physically reasonable image transformation to be assessed with greater certainty and a resulting image of good quality to be found. Further regularization terms and methods are known from mathematics and can likewise be used here. In place of a regularization term, certain models of potential deformations may also be implemented within the framework of the image varying function 22, e.g. if this function only allows certain image changes, The regularization term may not only depend on the image transformation function T or the parameters thereof, but additionally on further parameters, such as the transformed image T(V) itself or the history of the previous transformations. The regularization term may also include models of the image. Such models may be implemented as so-called Finite Element Models (FEM). Finite Volume Models (FVM), Statistical Shape Models, and Statistical Deformation Models. Examples of a regularization term will be mentioned hereinafter together with possible image transformations T.

A termination condition may be implemented in addition. If, for instance, an image quality value calculated by the image quality functional is too low and/or an acceptable value requires an unrealistic image deformation, this can cause the output of a warning signal.

The image varying function 22, T(V) may for example be implemented as follows: the original nuclear image 10 is first segmented (divided) into partial volumes by means of a segmenting function. This segmenting may be done according to a fixed rule (such as in s³ equally sized partial volumes of the sizes X/s*Y/s*Z/s) or as a function of image recognition and/or an anatomic body model, which recognizes and segments certain body parts as a whole for example. Such image segmenting algorithms are so-called region growing, level set, snakes, histogram-based, atlas-based, graph-based or similar segmenting algorithms. The image varying function 22 is then configured to apply at least one or more operations to each or at least some of these partial volumes, depending on the respective parameters. Such operations may be selected from the following group: rotating, shifting, stretching/compressing, distorting, shearing, or a mixture thereof.

In a simple but already useful example, the image varying function 22 for instance only allows the respective partial volumes to be shifted independently of each other. In this case the transformation can be described by means of a set of displacement vectors $t_1 \ldots t_m$ (one vector for each of m displaceable partial volumes). In a more complicated example, the boundary regions of the partial volumes are also deformed (extended or compressed), depending on the displacement, in such a manner that the boundary voxels of adjacent partial volumes are not displaced too much with respect to each other.

A similar effect may also be achieved by means of a regularization term which includes a summand $f(t_k,t_l)=(t_k-t_l)^2$ for each pair of the adjacent partial volumes k, l, which acts like an elastic spring and suppresses displacements that deviate too much from each other:

$$R(T) = c^* \Sigma_{i,j}(t_k-t_l)^2$$

More generally and according to a general aspect, the image quality functional may thus include an error term (consistency term) and a regularization term, with the error term depending (at least indirectly) on the varied nuclear image, the nuclear radiation values and the detector coordinates, and expressing a consistency (hence the quality of concordance or inconsistency) between the varied nuclear image and the nuclear radiation values, the regularization term at least depending (at least indirectly, e.g. via variation parameters) on the varied nuclear image and expressing the plausibility of the varied image.

Merely a simple displacement or rotation of the nuclear image as a whole is not yet regarded as an image varying function since in this case the nuclear image is not varied in the true sense of the word. A more complex change of the nuclear image, at least a compression, extension or segmentation in at least two partial volumes, and the at least partial independent displacement thereof is required.

Figure 8:
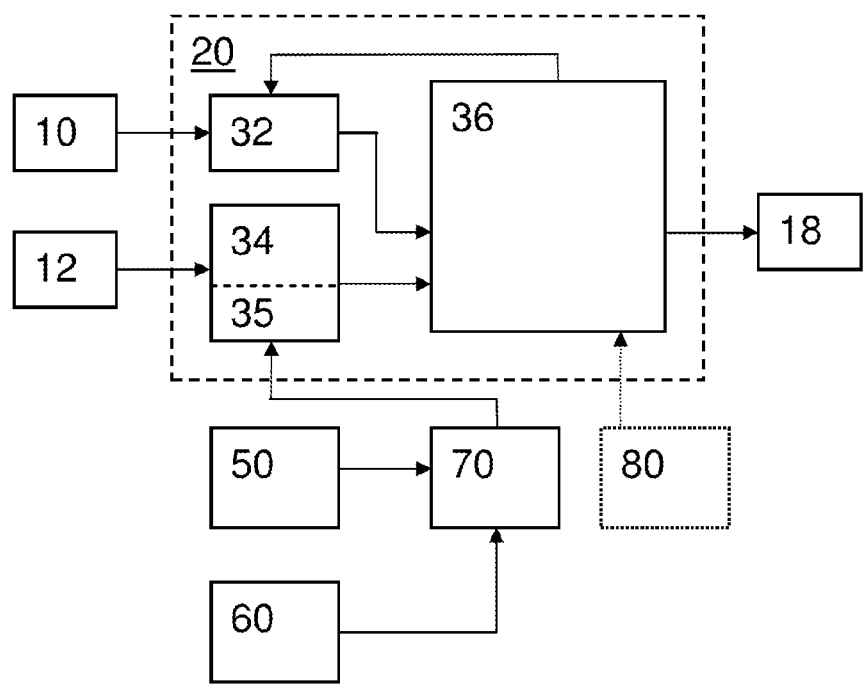
FIG. 8 shows a diagrammatic representation of the functionality of an image updating module of the nuclear image system of FIG. 7.

According to a further embodiment of the image updating module 20, the same can also comprise an image reconstruction algorithm 36 as shown in FIG. 8. The image reconstruction algorithm 36 receives the nuclear image 10 as a start image or start vector (input 32), and applies to it at least several steps of an iterative image reconstruction method for reconstructing a reconstructed nuclear image from the original nuclear image as a start image. In doing so, the image reconstruction algorithm 36 uses at least part of the measured data 12 (data 34) used to reconstruct the original nuclear image on the one hand, in addition, however, the nuclear radiation values 35 from the nuclear radiation detector 50 and the detector coordinates from the tracking system 60. After a number of iteration steps, the reconstructed nuclear image is then output as the updated nuclear image 18. Such an iterative image reconstruction method of the image reconstruction algorithm 36 may likewise be performed, based on the iterative varying of the nuclear image 32, by means of an image varying function or an image quality functional.

Figure 9:
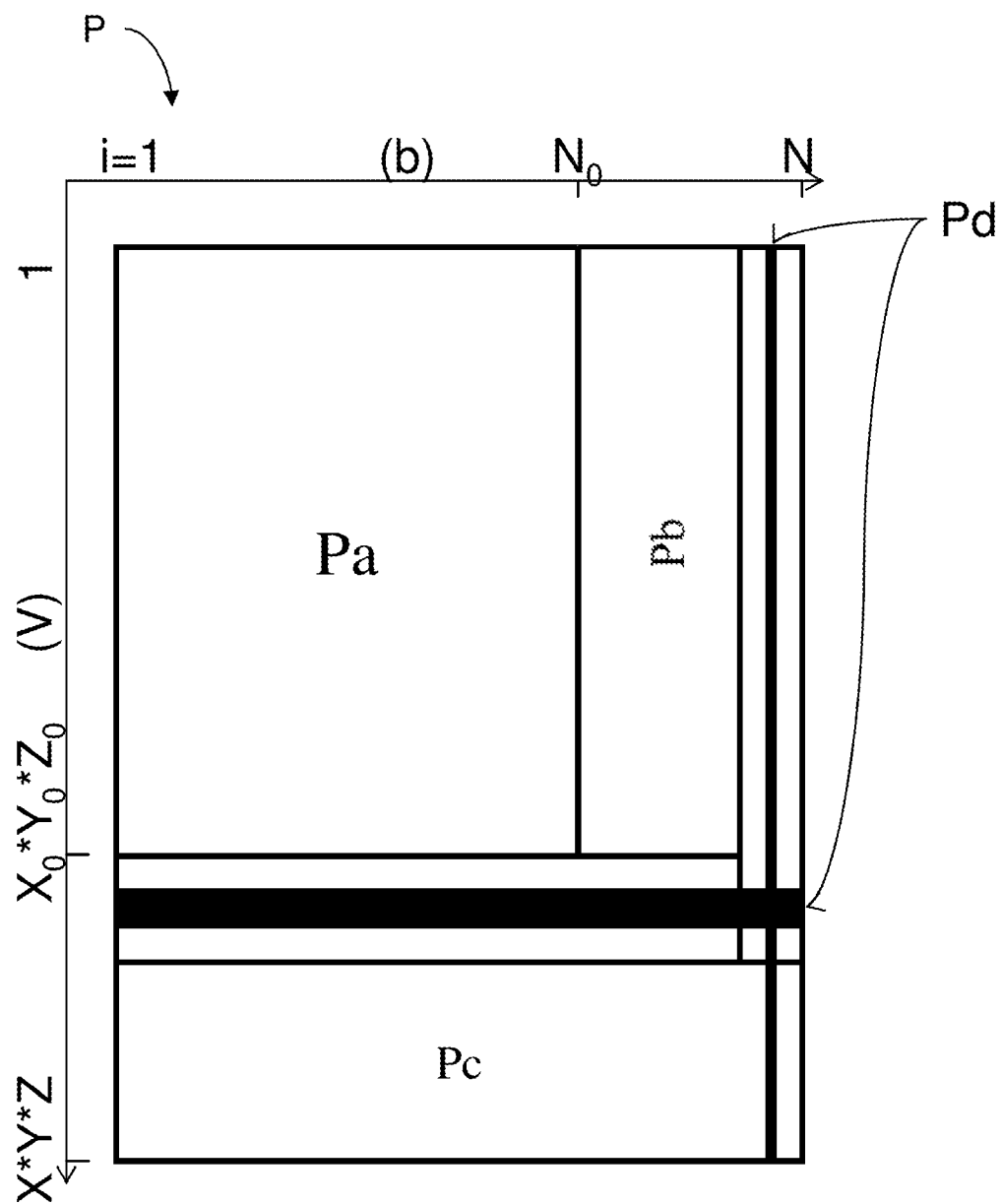
FIG. 9 shows a schematic view of a projection mapping for the nuclear image system of FIG. 7.

FIG. 9 illustrates the optional functionality of the described image reconstruction algorithm in further detail. According to this functionality, the original nuclear image (radiation distribution $V_0$ with $X_0*Y_0*Z_0$ voxels) was obtained from $N_0$ original measured data. This nuclear image is now to be updated by means of new, additional nuclear data (N-$N_0$ nuclear radiation values including the associated posture of the nuclear radiation detector). In this case, the number of voxels may be increased optionally since the additional measurements may allow higher spatial resolution or an enlarged VOI (volume of interest).

The already mentioned projection mapping P is illustrated as a matrix in FIG. 9. As described above, the mapping P for the nuclear image V outputs the associated simulated nuclear data b=P(V) to be measured from a detector having postures p. P is a linear mapping and may therefore be represented as a matrix. The values of the matrix B result from the postures p of the detector by means of a geometric model of the measurement environment.

The matrix P may be subdivided into partial regions Pa, Pb and Pd for all the nuclear radiation values (nuclear radiation values of the original nuclear image and new additional radiation values. Pa is the partial matrix allocated to the original nuclear image: for a given intensity distribution (original nuclear image) $V_0$ ($X_0*Y_0*Z_0$ voxels in the coordinate system of the original nuclear image), this matrix renders associated simulated nuclear data $b_0$=Pa($V_0$), which would be expected in the original measurement ($N_0$ measurements). The entries of the matrix Pa depend on the posture p of the detector in the original measurement. Hence the original nuclear image $V_0$ may be obtained by approximately solving the equation $b_0$=Pa($V_0$), with $b_0$ as the (approximately) actually obtained nuclear data, or by minimizing the corresponding functional from eq. (1) above.

In one embodiment, the new, additional nuclear radiation values may be employed together with and in the same way as the original radiation values, so as to reconstruct the radiation distribution. If the coordinate system remains unchanged for the radiation distribution ($X_0*Y_0*Z_0$ voxels), this will merely lead to an expansion of the matrix by the partial matrix Pb since the reconstruction is now performed on the basis of N rather than $N_0$ measurements. Optionally, parts of the original measurements can be removed as will be described further below with respect to Pd.

For better spatial resolution or enlargement of the volume, the additional measurements may optionally contribute to an increase in voxels of the radiation distribution. In this case, the number of lines of the matrix P increases to X*Y*Z lines (=dimension of the output vector V). This increase may also be utilized to reduce the over-determination of the equation to be solved and thus be utilized to reduce artefacts. In this case, further partial matrixes Pc accrue to matrix P.

The updated nuclear image (updated intensity distribution) may then be obtained analogously to the original nuclear image by reconstruction, e.g. by the (approximate) extremal value formation of the functional defined in eq. (1) for the matrix P. In doing so, an iterative method as described above may be used for minimizing purposes. In the iterative method, an arbitrarily selected start vector may be used. For instance a start vector may be used, which was generated during the use of the original nuclear image for example, which includes the original nuclear image as entries allocated to partial matrix Pa (first $X_0*Y_0*Z_0$ entries). The additional entries of the start vector may be random values for example.

Optionally, the size of the matrix may be reduced by deleting selected lines and/or columns of the matrix P (matrix section Pd). In other words, image sections of the radiation distribution (lines of matrix P) are omitted or combined, and/or nuclear radiation values (columns of matrix P) are omitted or combined. This enables the calculation to be accelerated.

For instance, according to a possible general aspect one or more of the following criteria for omitting or combining image sections of the radiation distribution (lines of matrix P) may be applied according to the updating rule:
  the significance of the measured nuclear radiation values is low for these image sections (the norm for the line vectors of the matrix P falls below a predetermined limit value);
  the image sections are outside the predetermined VOI (volume of interest);
  the significance of the nuclear radiation values is not sufficient for the image section (no posture of the nuclear radiation values satisfies a predetermined reference criterion in relation to the image section, and/or the norm for the respective line of the matrix P falls below a predetermined limit value).

For instance, according to a further possible general aspect, one or more of the following criteria for omitting or combining image sections of the radiation distribution (columns of the matrix P) may be applied according to the updating rule:
  the significance of these nuclear radiation values is low for all image sections to be mapped (the norm for the column vector of the matrix P fall below a predetermined limit value);
  the significance of one of the nuclear radiation values or a combination of nuclear radiation values is similar to the significance of another of the nuclear radiation values or another combination of nuclear radiation values (the norm for a linear combination of the column vectors of the matrix P falls below a predetermined limit value);

the posture of these nuclear radiation values satisfies a predetermined omission or combination criterion;

the point of time when the nuclear radiation values were measured, dates back longer than a predetermined time;

a(n) (identically or differently weighted) combination of these criteria.

Examples of a predetermined omission or combination criterion are illustrated in FIG. 10. FIG. 10 schematically shows the trajectory 7 of the nuclear radiation detector and the detector coordinates (posture) 6 in the respective nuclear measurements. In this case the detector coordinates 6 are illustrated by respective arrows whose base points symbolize the detector locations and whose directions symbolize the detector's solid angles in the respective measurements.

Group 6a forms a group of three very similar detector coordinates (postures), for which very similar column entries for matrix P are consequently expected. In order to reduce the calculation time, the three associated measurements can be combined in one measurement. This is achieved by a comparing the postures of the measurements and then combining similar postures (the norm for the difference in the postures is smaller than a predetermined limit value).

A similar criterion leads to the same result: the comparable postures lead to similar columns of the P matrix. Therefore, similar columns of the P matrix may be combined. More generally, columns of the P matrix exhibiting a linear combination may be combined, for which the norm is smaller than a predetermined limit value. Thereby the over-determination of the equation system to be solved may be avoided.

Another omission criterion relates to the posture 6b: very few measurements with a similar posture are available here, and for the associated image section (voxels of the radiation distribution), the equation system is under-determined and therefore not capable of a stable solution. This criterion may be used to omit or combine voxels. Those voxels which do not exhibit sufficient causal relationships to any of the postures may be omitted. The sufficient causal relationship may either be assessed geometrically, e.g. each voxel at which a posture vector 6 is sufficiently directed is marked, and voxels which are not or not sufficiently marked are eliminated. Alternatively or additionally, voxels can be eliminated, whose line vectors of the matrix P fall below a predetermined norm.

The criterion illustrated by posture 6b may also be employed as an omission criterion for nuclear data: measurements in which the detector was moved at a high speed may be omitted for instance, since poor data quality is expected in these measurements. At equal measurement intervals, the detector speed may be expressed by the (norm for the) difference between the postures of two temporally adjacent measurements. If the difference exceeds a predetermined limit value, the corresponding measurement is omitted.

Hereinafter, further embodiments will be described with reference to FIGS. 2 to 7. The embodiments are similar to the FIG. 1 embodiment and to each other, and identical reference numbers refer to identical components. Apart from the deviations described below, the description of the remaining Figures may also be referred to for the respective, described Figures.

Figure 2:
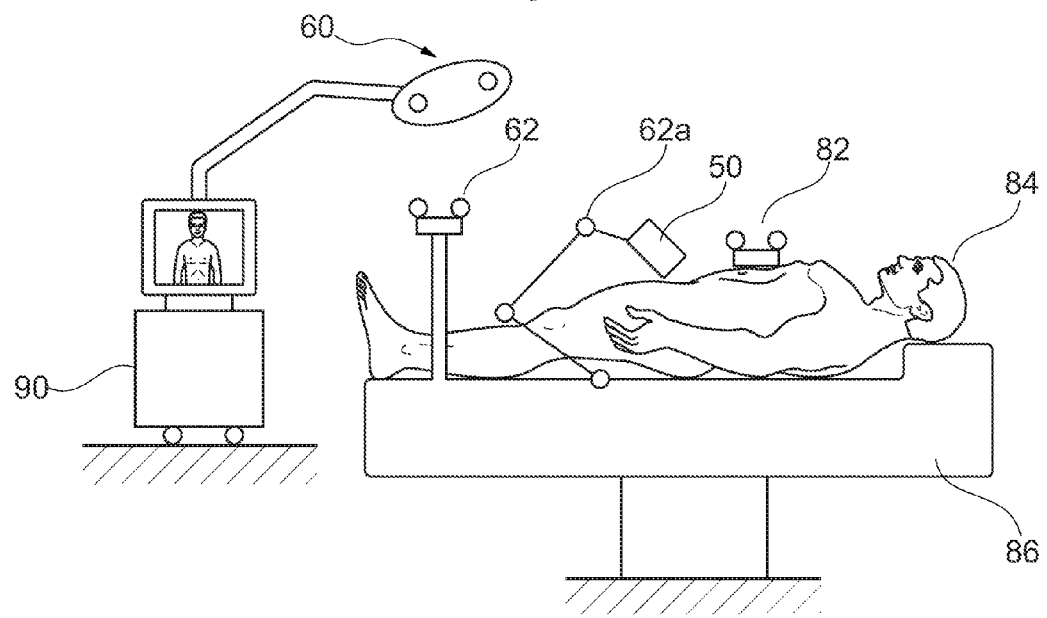
FIG. 2 shows components of a nuclear image system according to an embodiment of the invention.

The nuclear detector 50 of FIG. 2 is not directly but only indirectly connected to a tracking target object 62 via a mechanical tracking system 62a. This mechanical tracking system 62a connects the detector 50 via a series of arms to a reference body, the bed 86 for the person 84 to be imaged. The arms of the tracking system 62a are interconnected by articulations, such that the detector is freely movable (i.e. at least within a determined volume in all three spatial directions, and may even be freely rotated here). At the same time, the arms hold the detector in a defined position even when it is released.

The deflection of the tracking system 62a articulations is detected and thus the posture relative to the reference body 86 tracked. In turn the reference body 86 is connected fixedly to the tracking target object 62. Ultimately, the same is achieved in FIG. 2 as is achieved in FIG. 1, namely a relative posture determined between the nuclear detector (coordinate system KD) on the one hand and the tracking target object 82 (coordinate system ND) attached to the patient.

Figure 3:
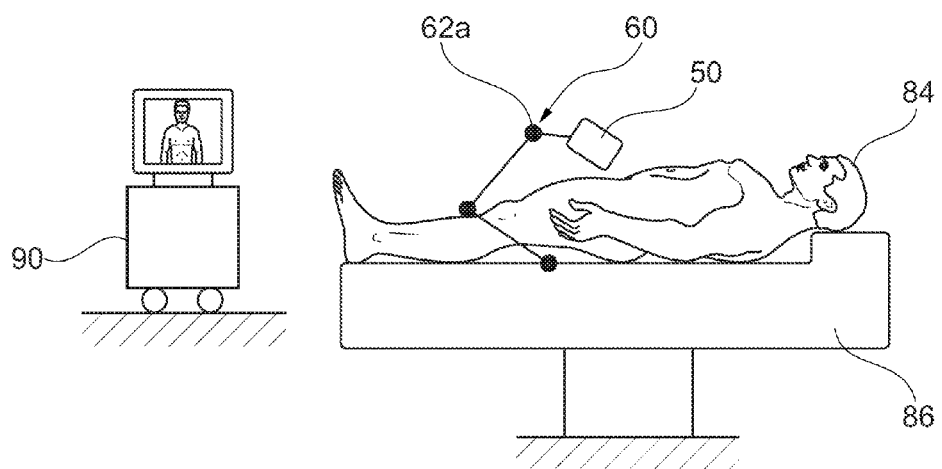
FIGS. 3 to 6 show components of nuclear image systems according to further embodiments of the invention.

With the nuclear detector of FIG. 3, the relative posture of the nuclear detector to the bed 86 is determined via the mechanical tracking system 62a. The person to be imaged lies in a predetermined position on the bed 86 or is fixed thereto, such that a fixed position of the nuclear image coordinate system KN to the bed 86 may be assumed. Thus the tracking system 62a allows in turn a correlation between the detector coordinate system KD and the nuclear image coordinate system KN.

The FIG. 3 embodiment has the disadvantage that positional changes of the patient can only be recognized indirectly from the nuclear data (via the image quality functional). This disadvantage may be reduced according to a general aspect as follows: a localizing module localizes at least one reference body point of the person 84 to be imaged, relative to the image coordinate system KN, preferably during or immediately before/after measuring the nuclear radiation, so that a substantial positional change of the person 84 is not to be expected. This localization does not need to take place in the coordinates of the image coordinate system. This localization may then enable the at least one reference body point to be registered with a corresponding point in the nuclear image (radiation distribution image) and thus allow for even more reliable allocation.

According to one example, further positional data depending on the position of the person 84 to be imaged is collected and the original nuclear image (radiation distribution image) pre-transformed, based on this positional data. Whenever the person 84 to be imaged is mentioned, this must not necessarily refer to the entire person but may also refer to only a part of that person. For example, the positional data may even reflect the position of only a part of the person to be imaged rather than of his/her entire body.

In a variation of the FIG. 3 embodiment according to this aspect, a supporting surface of bed 86 is equipped for example with weight sensors. The weight sensors supply weight distribution data reflecting the weight distribution of the person 84 to be imaged. By comparing this data to corresponding weight distributions measured during the recording of the original nuclear image for example, an image pre-processor can now recognize a positional change and pre-transform the nuclear image accordingly (e.g. displace the nuclear image, to be more precise, the radiation distribution image as a whole or parts thereof according to the displacement of the center of gravity or the displacement of contact pressure points).

Alternatively or additionally, the image quality functional exhibits the dependence of this positional data. This is shown in FIG. 7 as an optional variant according to which the image quality functional 24 is operatively connected to the localizing module 80, in order to receive localizing data of the reference body point. Positional data from the localizing module 80 are entered into the image quality functional 24 and used to calculate the image quality value.

According to this aspect, such image transformations for example may be preferred by means of a further summand, which transformations provide good concordance with respect to the positional data (e.g. the weight distribution). Such a summand may for instance be proportional to the L2 norm for the difference between the original positional data, (obtained during the recording of the original nuclear image) co-transformed with the nuclear image, and the current positional data, whereby both positional data are represented by a vector.

In an analogous manner, instead of the weight distribution or additionally thereto, the position in space of a body surface of the person 84 (e.g. a distinctive or structured body surface, such as in the neck or axillary region—it does not have to be the entire body surface of the person 85), may be used as positional data. This body surface position may be determined by a surface determining system and subsequently used for pre-transformation or image regularization. The body surface may be determined in a scanning mode by means of mechanical scanning by a tracked scanning object, which may be identical to the nuclear detector 50, or by means of another instrument for determining the position of a surface. Such an instrument may for example also be a time-of-flight camera, a stereoscopic camera, a laser scanner or a combination thereof. For determining the position of the surface, the tracking system may be employed directly for example. In that one or more tracking target objects or marks (fiducials) are mounted thereto. Commercially available systems, such as the Kinect system for instance, may also be used to determine the surface or positional data.

An image evaluating system for evaluating at least one distinctive feature (so-called landmark) in the nuclear image (to be more precise, the radiation distribution image) or in an additional image, e.g. an optical image or an additionally generated sectional image, such as US, CT, MR, may be used in an analogous manner. These are suitable for determining positional data and may be used as described above.

Hence the image quality functional 24 includes a localizing term according to one aspect, which expresses concordance of the reference body point(s) localized by the localizing module 80 with the nuclear image (to be more precise, the radiation distribution image). This localizing term may be embodied as a part of the consistency term or the regularization term or as an additional term.

Figure 4:
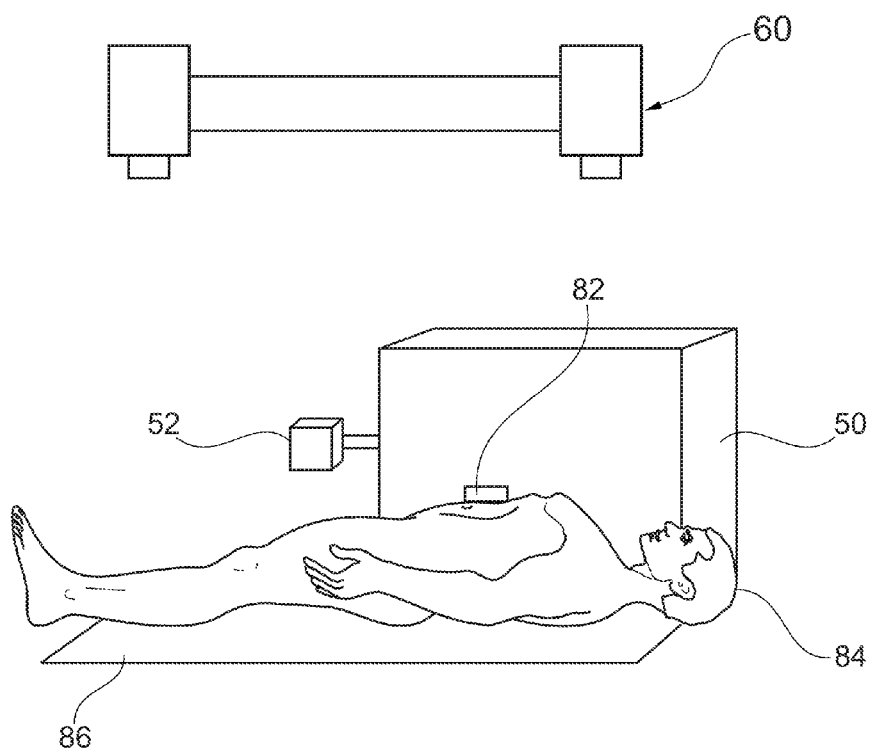

In the further embodiment of FIG. 4, a high-energy gamma camera for PET applications is mounted on one side. The original nuclear image is obtained by means of PET imaging (by the two-dimensional detector 50) and a further detector for detecting coincidences, not shown in the Figure. This further detector may be configured analogous to the FIG. 1 detector 60 and in particular be freely movable. Additionally, the positional data of the patient is determined in fact by the following submodules described above in more detail with reference to FIG. 3:

a supporting surface 86 including weight sensors;
a stereoscopic camera 60 as a surface determining system; and
a tracking target object 82 attached to person 84.

Additionally, the nuclear detector 40 is likewise tracked by a tracking target object 52 attached fixedly thereto. The nuclear detector may therefore be moved freely and a relationship between the tracking coordinate system and the detector coordinate system still be maintained. If necessary, the nuclear detector may also be completely removed after the original nuclear image has been taken.

Here as well, the nuclear image or radiation distribution image may be iteratively varied as described above, by means of the image updating module, so as to approximate the minimum of the image quality functional. The image quality functional may for example include the deviation between the original (i.e. obtained when generating the original nuclear image) positional data, co-transformed with the nuclear image, and the current positional data of the localizing submodules. A term comparable to $\|P(p,T(V))-b\|_{L2}$ may even be omitted. An additional regularization term may be included optionally.

The tracking system 60 in FIG. 4 is an electromagnetic tracking system. However, any other tracking system may be used.

Figure 5:
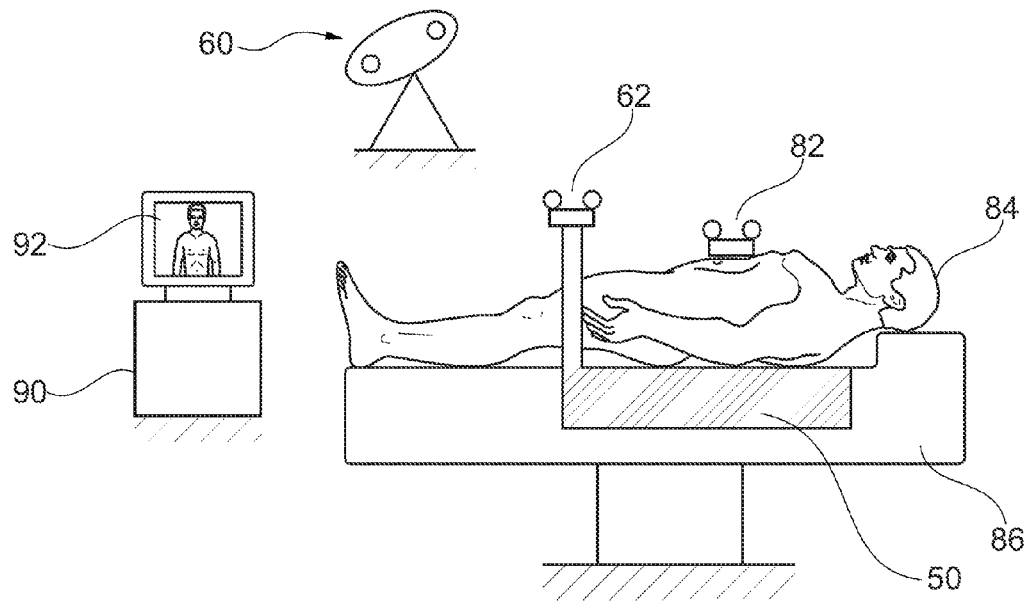

In principle, FIG. 5 corresponds to FIG. 4; here, however, the nuclear detector 50 is integrated into the bed 86 and used for nuclear image generation. The nuclear detector 50 may be used for the original nuclear image and additionally deliver updated nuclear measurements which are used for an updating similar to that in FIG. 1. Similar to the FIG. 4 detector, this detector 50 is also tracked by a tracking target object 62 connected fixedly to the bed 86, in this case by means of the optical tracking system 60. A freely movable detector may be used in addition, to allow for different visual angles, either analogously to the description of FIG. 4 by means of a PET method using both detectors, or as an additional detector, analogous to FIG. 1.

Here, only the tracking target object 82 attached to the patient 84 for generating positional data, which may be used by the localizing module to update the nuclear image, is illustrated, but the herein described remaining positional data may also be used in addition.

In all of the FIGS. 1 to 5 moreover a screen for outputting the updated nuclear image 92 and, if need be, additional information is shown. The system 90 renders the updated nuclear image (to be more precise, the radiation distribution image) in real time (to be more precise, almost real time) on the screen 92. Real time means that the image is continuously updated on the basis of measurements just obtained. This is possible because the complete reconstruction of the image does not need to be performed and fewer measurements are required or must be taken into account than for the complete reconstruction of the image.

Figure 6:
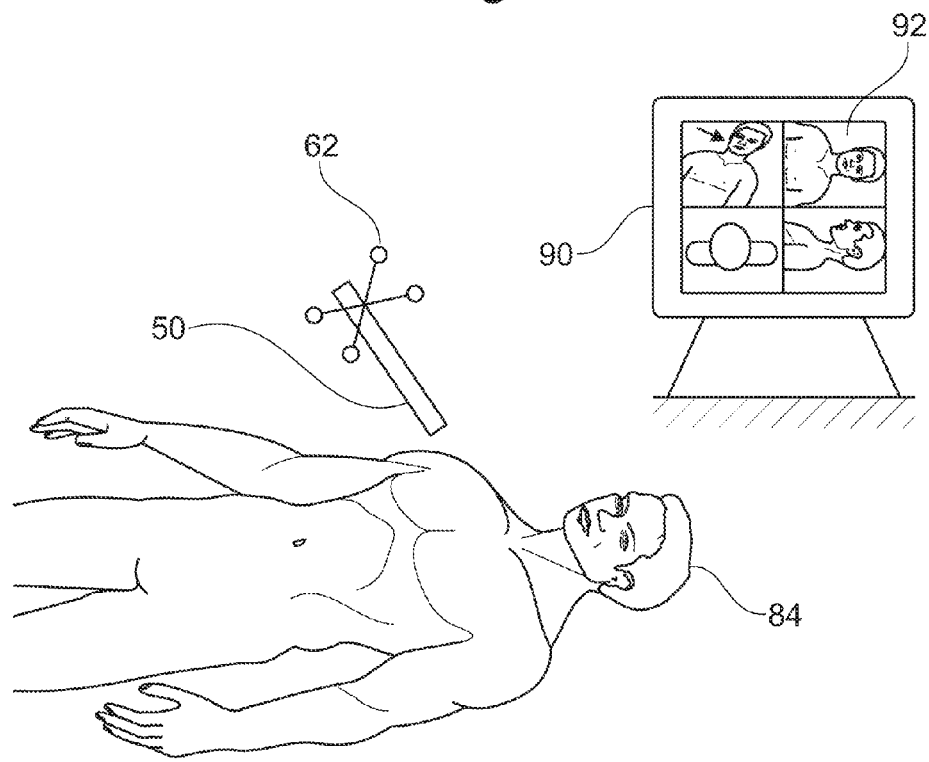

This screen is illustrated in more detail in FIG. 6. Since the updated nuclear image (to be more precise, the radiation distribution image), as well as the original nuclear image, is a complete three-dimensional image, different perspectives or sections may be represented, so as to convey three-dimensional image information.

Additionally, further information may be displayed, such as expanded reality information and/or information to guide the nuclear probe, to obtain improved measured data. The obtaining of such information is described for example in the patent applications DE 10 2010 017 543 and DE 10 2009 042 712, the contents of which are incorporated herein by reference.

Instead of the tracking systems 60, 62a illustrated in FIGS. 1 to 5, various tracking systems for determining detector posture may be used as a general aspect, for example an electromagnetic, optical, mechanical (passive or active, e.g. mounted to a controllable robot arm) tracking system. The tracking system may also be realized by a camera mounted fixedly to the gamma probe and aiming at stationary tracking target objects. Also, a tracking system may be realized by an acceleration sensor and gyroscope integrated into the nuclear detector 50.

A method for updating an original nuclear image will now be explained with reference to FIG. 11. The method comprises the following steps:

S1: starting the method;

S2: performing an original measurement of a nuclear radiation;

S3: reconstructing an original nuclear image from the nuclear radiation measured in S2: An original nuclear image is thus obtained in steps S2, S3. This original nuclear image is a complete three-dimensional nuclear image. i.e. it is finished and may be displayed directly, to visualize the radiation distribution.

S4: After the completion of the original nuclear image, measuring nuclear radiation by means of a nuclear radiation detector, which is freely movable along a freely variable path, so as to obtain nuclear radiation values, and tracking the nuclear radiation detector while measuring the nuclear radiation, so that detector coordinates are obtained, which indicate the posture of the tracked nuclear radiation detector in a reference coordinate system;

S5: associating the nuclear radiation values with respective ones of the detector coordinates;

S6: generating an updated three-dimensional nuclear image by applying an updating rule to the original nuclear image, with the updating rule changing the original nuclear image on the basis of the nuclear radiation values and the detector coordinates.

The original nuclear image includes at least a partial mapping of the person to be imaged. In step S4 the method may further include the localizing of at least one reference body point of the person to be imaged relative to the reference coordinate system.

FIG. 12 shows a diagram representing a quality value Q as a function of an iteration value x in the method of FIG. 11. In this case, the original nuclear image is represented in step S2 (see FIG. 11) by the matrix Pa shown in FIG. 9 and the original nuclear data $b_0$ (vector of length $N_0$), and the original radiation distribution image $V_0$ ($X_0 * Y_0 * Z_0$ voxels, original nuclear image in a more restricted sense) is obtained by minimizing the quality value Q of eq. (1), using the matrix Pa and the original data $b_0$.

The reconstructing of the original nuclear image (step S3) ensues by the minimizing of the quality value Q in an iterative method, e.g. the MLEM method (maximum likelihood expectation maximization). In this case, an arbitrary (e.g. randomly selected) start value is used for the original radiation distribution image $V_0$ and a minimum of eq. (1) iteratively approximated by means of the MLEM method. This minimizing is illustrated in the diagram of FIG. 12 during the interval $x_0 \ldots x_1.I$. For preventing artefacts from developing, the iterative method is stopped as soon as Q is sufficiently converged, even when further minimizing would be possible.

Thereafter, steps S4 and S5 are performed. Thus the user will see an image only when it is sufficiently converged. After that, the nuclear data b are updated as described above (now length N), and the matrix P is updated using the detector coordinates, i.e. brought into the form illustrated in FIG. 9.

In step S6, the radiation distribution image V (X*Y*Z voxels, updated nuclear image in a more restricted sense) is obtained by minimizing the quality value Q of eq. (1) using the matrix P and the updated nuclear data b. This in turn ensues by means of the iterative minimizing of the quality value Q described above, based on a start vector for V. In this case, the original result (nuclear image $V_0$) may be used as the start vector for the entries up to $V_0$, and the remaining entries may be arbitrary, e.g. random values. Alternatively, for all entries of the start vector for V, as well as for the entries up to $V_0$, arbitrary values may be used globally. The minimizing is illustrated in the diagram of FIG. 12 during the interval $x_0 \ldots x_2.I$.

Optionally, the updating rule may be applied several times or even iteratively. In FIG. 12 the updating rule is applied in an analogous manner as described at time $x_1$, also at further times $x_2$, $x_3$, etc. Thereby, the relative weight of the original image becomes lower and lower, and potential changes in the intensity distribution (movement of soft tissue, etc.) can be detected.

Image reconstruction allows an updated image to be displayed respectively at the times $x_1$, $x_2$, $x_3$, etc. The use of modern hardware and software (GPU-accelerated modern reconstruction algorithms such as MLEM) enables iteration within fractions of seconds even with low-cost standard PC components. This allows image updating within a few seconds (about 10 seconds per update).

Still further variants of a nuclear image system will be described hereinafter: According to one variant, a nuclear image system for updating an original nuclear image (10) comprises: a nuclear detector system (50) for generating a three-dimensional original nuclear image (10) which includes at least a partial mapping of the person (84) to be imaged; an original image localizing module configured to generate original positional data indicating the position of the person (84) to be imaged relative to the nuclear detector system (50), while generating the original nuclear image, a localizing module, which may be identical to or different from the original image localizing module, configured to generate current positional data indicating the position of the person (84) to be imaged, relative to the nuclear detector system (50) and at a later time after the generating of the original nuclear image; an image updating module (20) including an updating rule for changing the original nuclear image according to both the original positional data and the current positional data, with the image updating module being configured to generate an updated three-dimensional nuclear image (18) by applying the updating rue to the original nuclear image.

The method for updating an original nuclear image according to a further variant comprises: obtaining (S2, S3) the original three-dimensional nuclear image of a person (84) to be imaged; generating the original positional data indicating the position of the person (84) to be imaged relative to the nuclear detector system (50), while: generating the original nuclear image; thereafter generating the current positional data indicating the position of the person (84) to be mapped relative to the nuclear detector system (50) at a later time, after the generating of the original nuclear image; and generating (88) an updated three-dimensional nuclear image by applying an updating rule to the original nuclear image, with the updating rule changing the original nuclear image according to the original positional data and the current positional data. These variants may be combined with any other aspects described herein, in particular with the subject matters of the claims.

The invention claimed is:

1. A nuclear image system for updating an original nuclear image, the nuclear image system comprising:
   a data memory for storing the original three-dimensional nuclear image;
   a nuclear radiation detector, which is movable along a freely variable path, for measuring nuclear radiation, in order to obtain nuclear radiation values;
   a tracking system for tracking the nuclear radiation detector while measuring the nuclear radiation, so that detector coordinates are obtained which indicate a posture of the tracked nuclear radiation detector in relation to an image coordinate system of the nuclear image;

a nuclear data input configured to receive the nuclear radiation values from the nuclear radiation detector and the detector coordinates from the tracking system, and to associate the nuclear radiation values with the respective detector coordinates; and an image updating module including an updating rule for changing the original nuclear image on the basis of the nuclear radiation values and the detector coordinates, wherein the image updating module is configured to generate an updated three-dimensional nuclear image by applying the updating rule to the original nuclear image;

wherein the image updating module further comprises:

an image varying function for varying the nuclear image; and an image quality functional for calculating an image quality value from the nuclear radiation values and the varied nuclear image, wherein the image updating module is configured to vary iteratively the nuclear image by means of the image varying function, so that the image updating module calculates the nuclear image in a plurality of iterations such that the nuclear image gradually approximates an extremal value of the image quality functional, and to output the nuclear image resulting from the calculation as the updated nuclear image; and wherein the image quality functional includes a consistency term and a regularization term, wherein the consistency term depends on the varied nuclear image, the nuclear radiation values, and the detector coordinates, and expresses a consistency between the varied nuclear image and the nuclear radiation values; and wherein the regularization term depends at least on the varied nuclear image.

2. The nuclear image system according to claim 1, wherein the original nuclear image includes at least a partial mapping of a person to be imaged, the nuclear image system further comprising:

a localizing module configured to localize at least one reference body point of the person to be imaged relative to the image coordinate system.

3. The nuclear image system according to claim 2, wherein the localizing module preferably comprises at least one of the following:

(i) a marking element to be attached to the person to be imaged, wherein the tracking system is configured to obtain marking element coordinates which indicate a posture of the marking element;

(ii) a supporting surface with weight sensors, in order to determine a weight distribution of the person to be imaged, when the person is supine on the supporting surface;

(iii) a surface determining system for localizing a body surface of the person to be imaged; and (iv) an image evaluating system for evaluating at least one distinctive feature in the nuclear image or in an additional image.

4. The nuclear image system according to claim 3, wherein the image quality functional is operatively connected to the localizing module for receiving localizing data of the reference body point and for calculating the image quality values on the basis of the localizing data.

5. The nuclear image system according to claim 3, wherein the image varying function is configured to segment partial volumes of the nuclear image and to manipulate the partial volumes within the nuclear image.

6. The nuclear image system according to claim 1, wherein the nuclear radiation detector is a detector of dimension 0, 1 or 2.

7. A method for updating an original nuclear image, the method comprising:

obtaining the original nuclear image as a three-dimensional nuclear image;

thereafter measuring nuclear radiation by means of a nuclear radiation detector, which is movable along a freely variable path, in order to obtain nuclear radiation values;

tracking the nuclear radiation detector while measuring the nuclear radiation, so that detector coordinates are obtained which indicate a posture of the tracked nuclear radiation detector in a reference coordinate system;

allocating the nuclear radiation values to respective ones of the detector coordinates;

generating an updated three-dimensional nuclear image by applying an updating rule to the original nuclear image, wherein the updating rule changes the original nuclear image on the basis of the nuclear radiation values and the detector coordinates, wherein the updating rule further comprises an image quality functional for calculating an image quality value from the nuclear radiation values and a varied nuclear image, wherein the image updating module varies iteratively the nuclear image by means of the image varying function, so that the image updating module calculates the nuclear image in a plurality of iterations such that the nuclear image gradually approximates an extremal value of the image quality functional, outputting the nuclear image resulting from the calculation as the updated nuclear image;

wherein the image quality functional includes a consistency term and a regularization term, wherein the consistency term depends on the varied nuclear image, the nuclear radiation values, and the detector coordinates, and expresses a consistency between the varied nuclear image and the nuclear radiation values; and wherein the regularization term depends at least on the varied nuclear image.

* * * * *